United States Patent
Safabash

[19]

[11] Patent Number: 5,957,166
[45] Date of Patent: Sep. 28, 1999

[54] METHOD AND APPARATUS FOR DISPERSING FLUID INTO A MATERIAL

[75] Inventor: Jason H. Safabash, Redwood City, Calif.

[73] Assignee: Fusion Medical Technologies, Inc., Mountain View, Calif.

[21] Appl. No.: 08/876,269

[22] Filed: Jun. 16, 1997

[51] Int. Cl.⁶ ........................................... B01F 5/12
[52] U.S. Cl. ........................ 141/26; 141/2; 141/9; 141/27; 141/100; 141/329; 141/383; 366/130; 366/268
[58] Field of Search ........................ 141/2, 9, 25–27, 141/100, 329, 330, 383; 366/130, 167.1, 267, 268; 604/82, 83, 85, 416

[56] References Cited

U.S. PATENT DOCUMENTS

| | | | |
|---|---|---|---|
| 2,796,017 | 6/1957 | Schmidt | 141/244 |
| 2,893,331 | 7/1959 | Medlock | 366/267 |
| 2,954,769 | 10/1960 | Callahan et al. | 141/330 |
| 3,082,681 | 3/1963 | Petersen | 141/329 |
| 3,700,215 | 10/1972 | Hardman et al. | 366/268 |
| 3,872,867 | 3/1975 | Killinger | 141/329 |
| 4,046,145 | 9/1977 | Choksi | 141/27 |
| 4,469,153 | 9/1984 | Morisette | 141/364 |
| 4,611,641 | 9/1986 | Carter, Sr. | 141/100 |
| 4,743,229 | 5/1988 | Chu | 604/82 |
| 4,804,336 | 2/1989 | Zdeb et al. | 604/85 |
| 4,834,149 | 5/1989 | Fournier et al. | 141/329 |
| 4,834,152 | 5/1989 | Howson et al. | 141/329 |
| 4,850,978 | 7/1989 | Dubar et al. | 604/201 |
| 5,022,442 | 6/1991 | Bird | 141/100 |
| 5,088,996 | 2/1992 | Kopfer et al. | 141/329 |
| 5,158,558 | 10/1992 | Melker et al. | 141/329 |
| 5,352,036 | 10/1994 | Haber et al. | 366/130 |
| 5,423,753 | 6/1995 | Fowles | 604/85 |
| 5,425,580 | 6/1995 | Beller | 366/131 |
| 5,454,786 | 10/1995 | Harris | 604/416 |

FOREIGN PATENT DOCUMENTS

WO/9607472A1 3/1996 WIPO.

*Primary Examiner*—J. Casimer Jacyna
*Attorney, Agent, or Firm*—Townsend and Townsend and Crew LLP

[57] ABSTRACT

A fluid dispersion and delivery assembly (16) includes first and second syringes (18,20) containing a first, fluid material (32) and a second material (34), fluidly coupled together at their distal ends (22,24) by a fluid transfer assembly (2). The fluid transfer assembly includes a double Luer fitting (4) and an elongated, hollow, perforated tube (6) extending into the interior (26) of the second syringe. This permits the first, fluid material in the first syringe to be properly dispersed into the second material within the second syringe by simply pressing the plunger (28) of the first syringe. The sizing, spacing and positioning of the holes (14) in the tube can be adjusted to provide even or uneven fluid distribution within the second syringe. After dispersion, the fluid transfer assembly is dismounted from the second syringe to permit combined material (36) within the second syringe to be dispensed.

23 Claims, 2 Drawing Sheets

METHOD AND APPARATUS FOR DISPERSING FLUID INTO A MATERIAL

BACKGROUND OF THE INVENTION

The present invention relates generally to methods and devices for dispersing a first, fluid material into a second material. It is particularly useful for evenly dispersing a first, fluid material from a first syringe into a second material within a second syringe.

The use of two syringes to mix two substances and then dispense the mixture from one of the syringes is known. U.S. Pat. No. 3,700,215 to Hardman et al. illustrates the outlet nozzles of a pair of syringes connected by a coupler. A perforated mixing tube is slidably mounted within the coupler so that depressing the plunger on one syringe drives the contents of that syringe into the other syringe and simultaneously drives the perforated mixing tube into the other syringe. The plunger of the other syringe is then depressed causing the contents to be driven back into the first syringe. This process is repeated a desired number of times until the substances are appropriately mixed. U.S. Pat. No. 4,743,229 to Chu illustrates a pair of syringes coupled at their outlet nozzles. One of the syringes contains a fibrillar collagen which is injected into the second syringe which contains particulate mineral material. Excess air in the first syringe containing the particulate mineral material is expulsed through a porous piston which permits air, but not the mineral material, to pass through the piston. The collagen-mineral mixture is then dispensed from the second syringe as a collagen-based bone repair preparation.

The Chu patent shows a relatively simple system for combining two materials within the barrel of one syringe. However, the injected material is not necessarily evenly dispersed within the other material. Therefore, unless the materials are driven back and forth between the two syringes as is taught in the Hardman patent, neither good dispersion nor good mixing will likely occur. However, certain materials, such as the collagen/mineral preparation of the Chu patent, are not amenable to such flow back and forth between two syringes. Also, other preparations, such as certain insulin preparations, may be sensitive to mechanical agitation or an increase in temperature which could be created while being forced back through a relatively small orifice between the two syringes.

SUMMARY OF THE INVENTION

The present invention is directed to method and apparatus for dispersing a fluid into a material in a simple, efficient and effective manner. The invention is adaptable for use with conventional syringes; only the fluid transfer assembly used to join the two syringes need be specially constructed.

A fluid dispersion and delivery assembly includes first and second delivery devices, typically syringes, coupled by a fluid transfer assembly. The first syringe contains a fluid material. A second syringe contains a second material into which the first material is to be dispersed. While the dispersion is typically desired to be even, uneven dispersion of the first material can also be accommodated through the invention.

The fluid transfer assembly preferably includes a double Luer fitting and an elongated, hollow, perforated tube mounted to and extending from the fitting. The fitting is used to mount the distal or needle end of the two syringes to the fitting and thus to one another with the perforated tube extending into the interior of the second syringe. This permits the first, fluid material in the first syringe to be evenly dispersed into the second material within the second syringe by simply pressing the plunger on the first syringe. The sizes, spacing and pattern of the holes can be adjusted to provide even or uneven fluid distribution within the second syringe. Thereafter, the fluid transfer system is dismounted from the second syringe, or other delivery device, to permit from the second syringe, or other delivery device, to permit combined material within the second syringe to be administered.

An advantage of the present invention is that it permits the even or uneven distribution or dispersion of a fluid material into a second material using a simple fluid transfer assembly. In the preferred embodiment, the fluid transfer assembly is designed to be mounted to Luer fittings at the distal ends of first and second syringes. This makes it adaptable for use with conventional syringes, thus lowering cost and expanding use.

Several advantages accrue because no multiple, reciprocating plunger strokes need be used to provide the desired dispersion. First, only one of the two substances needs to be a fluid. Second, heating of heat-sensitive substances or mechanical damage to agitation-sensitive substances is prevented by the elimination of multiple reciprocating plunger strokes. Third, mixing of air into the combined material, which can occur when multiple reciprocations of the syringe plungers are undertaken, is reduced.

The present invention finds particular utility when used to disperse a diluent, such as a hemostatic solution, into a flowable gel material. Such materials can be used in filling tissue divots, tissue tracks, body cavities, surgical defects and the like to inhibit post-surgical spinal and other tissue adhesions. An example of such a material is disclosed in U.S. patent application Ser. No. 08/704,852 filed Aug. 27, 1996, the disclosure of which is incorporated by reference.

Other features and advantages of the invention will appear from the following description in which the preferred embodiment has been set forth in detail in conjunction with the accompanying drawings.

DESCRIPTION OF THE PREFERRED EMBODIMENTS

Figure 1:
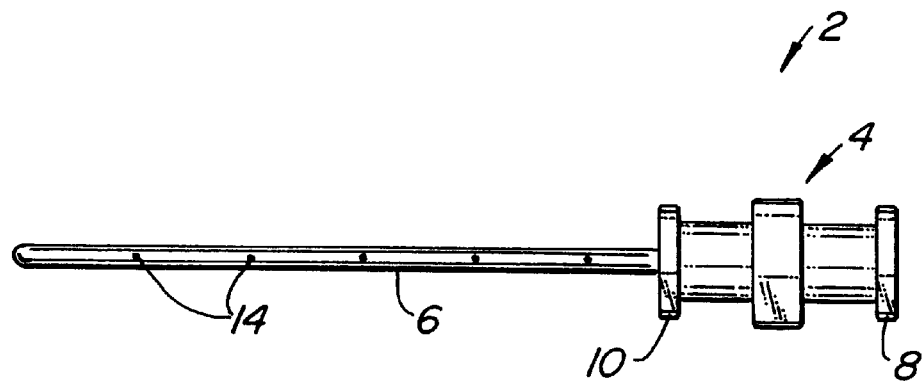
FIG. 1 is a side view of a fluid transfer assembly made according to the invention.

FIG. 1 illustrates a fluid transfer assembly 2 including double Luer fitting 4 and a perforated tube 6. Fitting 4 includes first and second Luer lock elements 8, 10 with perforated tube 6 extending past second Luer lock element 10. The enlarged proximal end 12 of perforated tube 6 extends generally to about the center of fitting 4. See FIGS. 2 and 2A. Fluid can pass through Luer lock element 8, through proximal end 12 of the perforated tube 6, along the interior of the perforated tube and out through a series of perforations 14 formed in the tube. Enlarged end 12 forms a fluid-tight seal within the interior of fitting 4 so that tube 6 provides the only fluid pathway through fitting 4.

Figure 2:
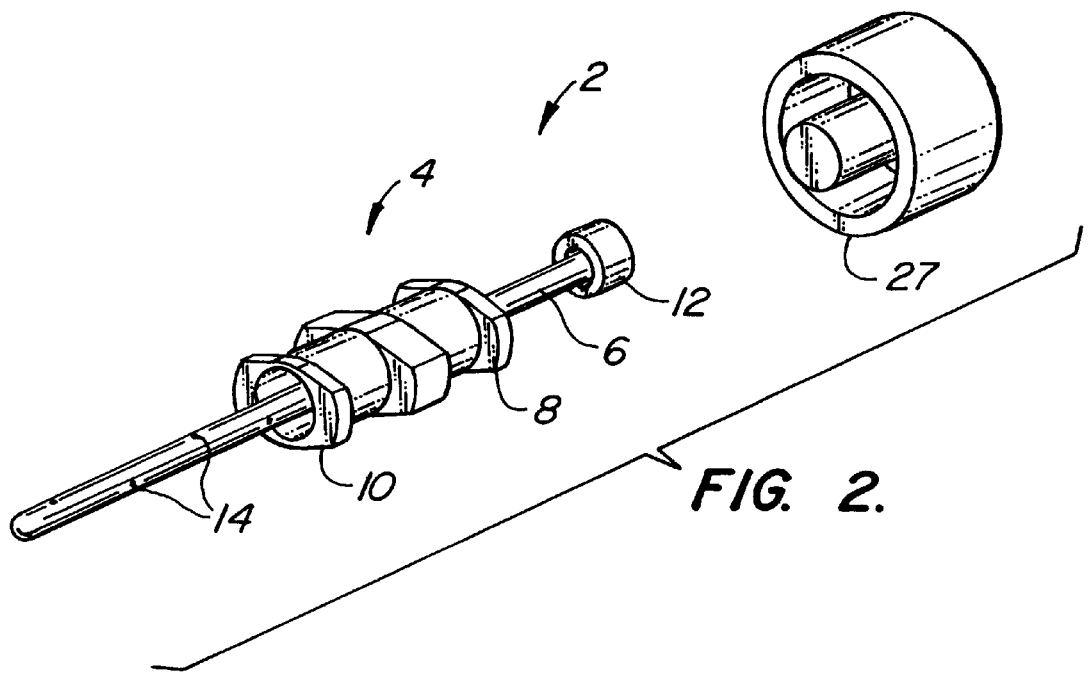
FIG. 2 is a partially exploded isometric view of the fluid transfer assembly of FIG. 1 and a mounting plug.
Figure 2A:
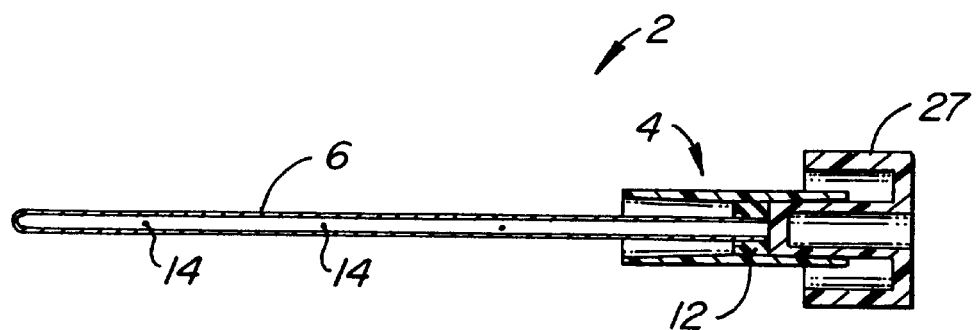
FIG. 2A is a cross-sectional view of the fluid transfer assembly of FIG. 1 with the mounting plug of FIG. 2 mounted thereto.
Figure 3:
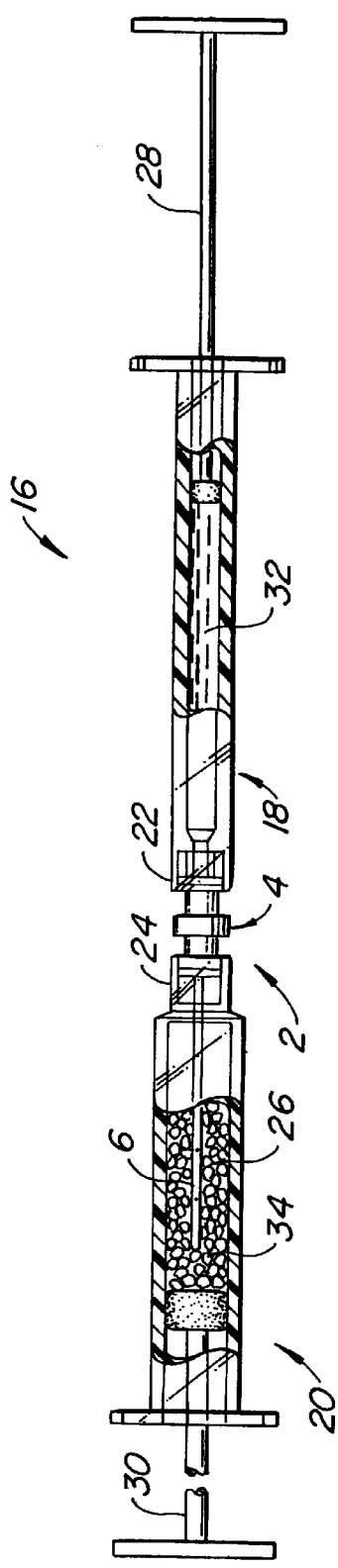
FIG. 3 is a partial cross-section view of a material preparation and delivery assembly, including the fluid transfer assembly of FIG. 1 coupling first and second syringes, before dispersion of the fluid within the first syringe.

FIG. 3 illustrates a material dispersion and delivery assembly 16, which includes fluid transfer assembly 2 and first and second syringes 18, 20. First and second syringes 18, 20 include first and second Luer fittings 22, 24 to permit fluid transfer assembly 2 to be used to couple first and second syringes 18, 20 to one another. When coupled as shown in FIG. 2, perforated tube 6 extends into the bore 26 of second syringe 20. FIGS. 2 and 2A illustrate a mounting plug 27 mountable to the hollow interior of Luer lock elements 8.

Assembly 16 of FIG. 3 is assembled in the following manner. Grasping mounting plug 27, the combination of FIG. 2A is mounted to Luer fitting 24 of second syringe 20 so that tube 6 extends into bore 26. Plug 27 is then pulled free of assembly 2. Luer fitting 22 of first syringe 18 is then mounted to first Luer lock element 8 resulting in assembly 16 of FIG. 3.

Bore 26 is initially partially filled with a second material 34, for example, a gel material in one embodiment, into which a first material 32 within first syringe 18 is to be dispersed. In one embodiment the material within first syringe 18 is a hemostatic solution.

Figure 4:
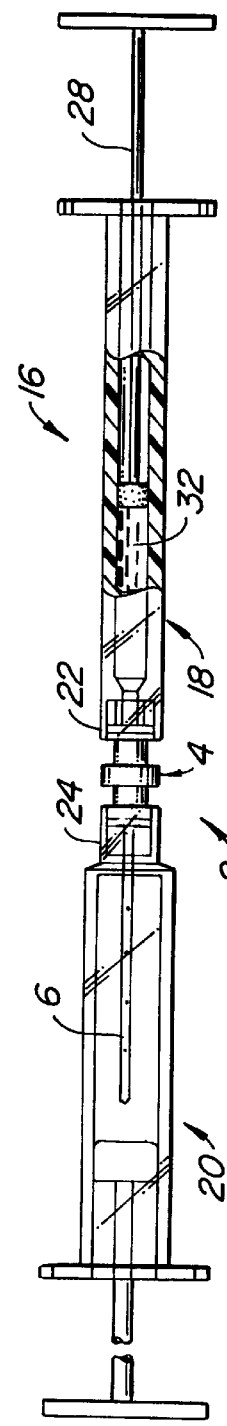
FIG. 4 shows the assembly of FIG. 3 mid-stroke.
Figure 5:
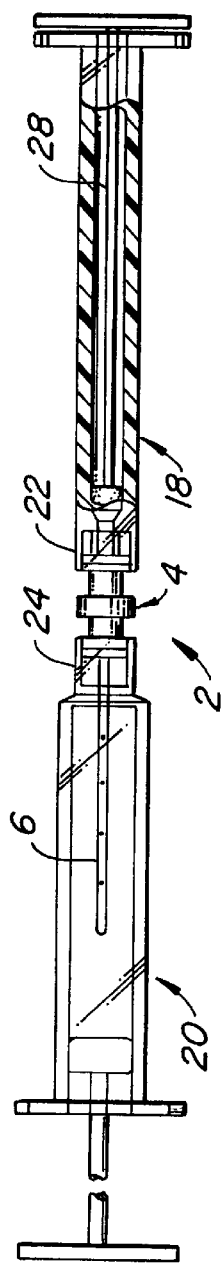
FIG. 5 shows the assembly of FIG. 3 at the end of the dispersion stroke with the fluid in the first syringe evenly dispersed within the material in the second syringe.

FIGS. 4 and 5 illustrate the relative orientations of the plungers 28,30 of first and second syringes 18, 20 as first plunger is depressed causing first material 32 to be directed into bore 26 and dispersed within first material 32. In the preferred embodiment, perforations 14 are sized, positioned, and spaced so that a generally even distribution of first material 32 is achieved within second material 34. However, depending on the circumstances, an uneven distribution of first and second materials 32, 34 may be desired. In such event, this can be accommodated by, for example, the appropriate modification of the size, spacing, and positioning of perforations 14.

After first material 32 is dispersed within second material 34, the materials become effectively thoroughly mixed because of the affinity of second material 34 for first material 32. This eliminates the need for further mixing or agitation steps. The combined material 36 can be dispensed by second syringe 20 by simply uncoupling second Luer lock element 10 from second Luer fitting 24, removing perforated tube 6 from bore 26, adding any needed appropriately sized and configured needle or other dispensing element to second Luer fitting 24, and then depressing plunger 30 to dispense combined material 36.

In a preferred embodiment, perforated tube is sealed at its distal end, has an inner diameter of about 1.4 mm (0.056"), a length of about 5 cm (2") and about 12–15 perforations 14, each about 0.005 inch in diameter.

Modification and variation can be made to the disclosed embodiment without departing from the subject of the invention as defined in the following claims. While the invention is particularly useful for use with first and second syringes 18, 20, first syringe 18 could be replaced by, for example, a collapsible bellows-type of delivery device or a rachet drive delivery device; either of these could be mounted to first Luer lock element 8 and have its contents driven through fluid transfer assembly 2. The invention can be used with types of materials other than those discussed. For example, second material 34 could be a liquid or a granular solid instead of a fractured, flowable gel material.

Perforated tube 6 can be made in other manners, such as by using a sintered material having small pores through its body as opposed to discrete perforations. Perforated tube 6 could also be other than straight, such as corkscrew-shaped. Also, perforations 14 do not need to be uniform in size; for example, it may be advantageous to have larger holes at the most distal end, or vice versa, for uniform or non-uniform dispersion of material. The perforations may be longitudinally equally spaced apart, as in the disclosed embodiment, or not.

What is claimed is:

1. A method for dispersing a first, fluid material into a second material comprising the following steps:

providing a first delivery device defining a first interior containing a first fluid material and having a first distal end;

providing a second delivery device defining a second interior containing a second material and having a second distal end;

mounting a fluid transfer assembly to the second distal end, the fluid transfer assembly comprising an elongated, hollow, perforated member extending into the second interior, said perforated member providing the only fluid path into the second interior;

fluidly coupling the first interior with the second interior by connecting the first distal end to the fluid transfer assembly;

dispersing the first material into the second material through the perforated member to create a combined material, said perforated member remaining generally stationary with respect to said second delivery device during said dispersing step; and removing the fluid transfer assembly from the second delivery device.

2. The method according to claim 1 wherein the providing steps are carried out using first and second syringes as the first and second delivery devices.

3. The method according to claim 1 wherein the first delivery device providing step comprises the step of selecting a hemostatic solution as the first material.

4. The method according to claim 1 wherein the second delivery device providing step comprises the step of selecting a flowable gel material as the second material.

5. The method according to claim 1 wherein the dispersion step is carried out so the first material is generally equally dispersed within the second material.

6. The method according to claim 1 wherein fluidly coupling step is carried out using twist-lock fastening elements on the first distal end and on the fluid transfer assembly.

7. The method according to claim 1 wherein the fluid transfer assembly mounting step is carried out prior to the first delivery device providing step.

8. The method according to claim 1 wherein the fluid transfer assembly mounting step further comprises the step of selecting the perforated member to include discrete perforations.

9. The method according to claim 8 wherein the perforated member selecting step comprises the step of selecting a perforated member having a plurality of identically-sized perforations.

10. The method according to claim 8 wherein the perforated member selecting step comprises the step of selecting a perforated member having a plurality of generally longitudinally equally spaced-apart perforations.

11. The method for preparing and dispensing a combined material comprising the following steps:

providing a first delivery device defining a first interior containing a first fluid material and having a first distal end;

providing a second delivery device defining a second interior containing a second material and having a second distal end;

mounting a fluid transfer assembly to the second distal end, the fluid transfer assembly comprising an elongated, hollow, perforated member extending into the second interior, said perforated member providing the only fluid path into the second interior;

fluidly coupling the first interior with the second interior by connecting the first distal end to the fluid transfer assembly;

dispersing the first material into the second material through the perforated member to create a combined material, said perforated member remaining generally stationary with respect to the second interior during the step of dispersing the first material;

removing the fluid transfer assembly from the second delivery device; and dispensing the combined material from the second delivery device.

12. A method for dispersing a first, fluid material into a second material to create a combined material and dispensing the combined material comprising the following steps:

providing a first syringe comprising a first syringe body defining a first bore and containing a first fluid material, the first syringe body having a first distal end;

providing a second syringe with a fluid transfer assembly mounted thereto, the second syringe comprising a second syringe body defining a second bore containing a second material and having a second distal end and a plunger movably mounted within the second bore, the fluid transfer assembly mounted to the second distal end of the second syringe body, the fluid transfer assembly comprising an elongated, hollow, perforated member extending into the second bore;

fluidly coupling the first bore with the second bore by connecting the first distal end to the fluid transfer assembly, said perforated member providing the only fluid path between the first bore and the second bore;

dispersing the first material into the second material through the perforated member to create a combined material, said perforated member remaining generally stationary with respect to the second interior during the step of dispersing the first material;

said dispersing step carried out so the first material is generally equally dispersed from the perforated member along the second bore containing the second material;

removing the fluid transfer assembly from the second syringe;

mounting a needle cannula to the second distal end of the second syringe; and dispensing the combined material from the second syringe through the needle cannula.

13. A fluid dispersion and delivery assembly comprising:

a first delivery device having a first interior capable of containing a first, fluid material, the first delivery device comprising a first port opening into the first interior;

a second delivery device having a second interior capable of containing a second material, the second delivery device comprising a second port opening into the second interior; and a fluid transfer assembly comprising:

a fitting removably mounting the first and second ports to one another;

an elongated, hollow, perforated member extending from the fitting and extending into the second interior, said perforated member being generally stationary with respect to the second interior; and the fluid transfer assembly defining a single fluid pathway from the first port, through the fitting, through the perforated member and into the second interior;

whereby the first material can be dispersed into the second material to create a combined material, the fluid transfer assembly can be dismounted from the second port and the combined material can be dispensed from the second delivery device.

14. The assembly according to claim 13 wherein the first delivery device comprises a syringe.

15. The assembly according to claim 13 wherein the second delivery device comprises a syringe.

16. The assembly according to claim 13 wherein the first delivery device is capable of containing a hemostatic solution as the first material.

17. The assembly according to claim 13 wherein the second delivery device is capable of containing a flowable gel material as the second material.

18. The assembly according to claim 13 wherein the perforated member comprises a hollow tube having axially spaced-apart access holes formed therein.

19. The assembly according to claim 18 wherein the access holes are generally equally-sized.

20. The assembly according to claim 18 wherein the access holes are generally longitudinally equally spaced-apart access holes.

21. The assembly according to claim 13 wherein the fitting comprises first and second twist-lock fittings for mounting to the first and second ports.

22. The assembly according to claim 13 wherein the elongated, hollow, perforated member is straight.

23. A fluid dispersion and delivery assembly comprising:

a first syringe having a first interior capable of containing a hemostatic solution, the first syringe comprising a first port opening into the first interior;

a second syringe having a second interior capable of containing a flowable gel material, the second syringe comprising a second port opening into the second interior;

a fluid transfer assembly comprising:

a fitting removably mounting the first and second ports to one another, the fitting comprising first and second twist-lock fittings for mounting to the first and second ports;

an elongated, hollow, perforated metal tube, having axially spaced-apart access holes formed therein, extending from the second twist-lock fitting and extending into the second interior; and the fluid transfer assembly defining a single fluid pathway from the first port, through the fitting, through the perforated tube and into the second interior;

whereby the hemostatic solution can be dispersed into the flowable gel material to create a combined material, said perforated member remaining generally stationary with respect to the second interior, and the fluid transfer assembly can be dismounted from the second port and the combined material can be dispensed from the second syringe.

* * * * *